United States Patent [19]

Mark

[11] 4,426,513
[45] Jan. 17, 1984

[54] POLYCARBONATE RESINS BASED ON POLYPHENOLIC COMPOUNDS

[75] Inventor: Victor Mark, Evansville, Ind.

[73] Assignee: General Electric Company, Mt. Vernon, Ind.

[21] Appl. No.: 44,039

[22] Filed: May 31, 1979

[51] Int. Cl.³ .............................................. C08G 63/62
[52] U.S. Cl. .................................. 528/204; 528/196; 528/201; 528/718
[58] Field of Search ........................ 528/201, 204, 196

[56] References Cited

U.S. PATENT DOCUMENTS

| | | | |
|---|---|---|---|
| 3,544,514 | 12/1970 | Schnell et al. | 528/204 |
| 3,799,953 | 3/1974 | Freitag et al. | 528/204 |
| 3,821,317 | 6/1974 | Webb et al. | 528/204 |
| 3,931,108 | 1/1976 | Binsack et al. | 528/204 |
| 4,001,183 | 1/1977 | Freitag et al. | 528/204 |

Primary Examiner—H. S. Cockeram
Attorney, Agent, or Firm—Martin B. Barancik

[57] ABSTRACT

Novel polyphenolic compounds are disclosed. These compounds have utility as branching agents in the production of novel, randomly branched polycarbonates

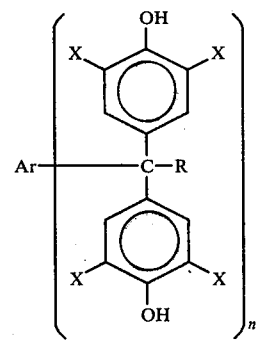

6 Claims, No Drawings

POLYCARBONATE RESINS BASED ON POLYPHENOLIC COMPOUNDS

This invention relates to novel polyphenolic compounds that have utility as branching agents and thermoplastic, randomly branched polycarbonates produced therefrom having excellent resistance to thermal oxidation and excellent blow molding properties and to a process for their preparation.

BACKGROUND OF THE INVENTION

Polycarbonates are well known, commercially important materials which are produced in large quantities. Such polymers are typically prepared by reacting a carbonate precursor with a dihydric phenol to provide a linear polymer consisting of units of the dihydric phenol linked to one another through carbonate linkages. These polymers have outstanding mechanical, thermal, and optical properties such as high tensile strength, optical clarity (transparency), thermal and dimensional stability and impact strength.

These aromatic polycarbonates differ from most thermoplastic polymers in their melt rheology behavior. Most thermoplastic polymers exhibit non-Newtonian flow characteristics over essentially all melt processing conditions. Newtonian flow is defined as the type of flow occurring in a liquid system where the rate of shear is directly proportional to the shearing force. However, in contrast to most thermoplastic polymers, polycarbonates prepared from dihydric phenols exhibit Newtonian flow at normal processing temperatures and shear rates below 300 reciprocal seconds.

Two other characteristics of molten thermoplastic polymers are considered to be significant for molding operations: melt elasticity and melt strength. Melt elasticity is the recovery of the elastic energy stored within the melt from distortion or orientation of the molecules by shearing stresses. Melt strength may be simply described as the tenacity of a molten strand and indicates the ability of the melt to support a stress. Both of these characteristics are important in extrusion blow molding, particularly in fabrication by extrusion blow molding. Non-Newtonian flow characteristics tend to impart melt elasticity and melt strength to polymers thus allowing their use in blow molding fabrication. In the usual blow molding operation, a tube of a molten thermoplastic is extruded vertically downward into a mold, followed by the introduction of a gas, such as air, into the tube thus forcing the molten plastic to conform to the shape of the mold. The length of the tube and the quantity of material forming the tube are limiting factors in determining the size and wall thickness of the objects that can be molded by this process. The fluidity of the melt obtained from bisphenol-A-polycarbonate, or the lack of melt strength as well as the paucity of extrudate swelling, serve to limit blow melting applications to relatively small, thin walled parts. Temperatures must generally be carefully controlled to prevent the extruded tube from falling away before it attains the desired length and the mold is closed around it for blowing. Consequently, the Newtonian behavior of polycarbonate resin melts has severely restricted their use in the production of large hollow bodies by conventional extrusion blow molding operations as well as the production of various other shapes by profile extrusion methods.

Thermoplastic randomly branched polycarbonates exhibit unique properties of non-Newtonian flow, melt elasticity and melt strength which permit them to be used to obtain such articles as bottles which were not heretofore easily or readily produced with linear polycarbonates. The thermoplastic, randomly branched polycarbonates can be prepared by reacting a polyfunctional compound containing three or more functional groups with a dihydric phenol and a carbonate precursor.

DESCRIPTION OF THE INVENTION

The novel compounds of the invention are polyphenolic compounds of the formula I:

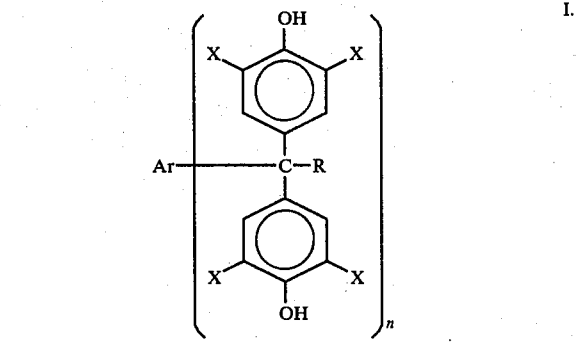

wherein Ar is either a substituted or unsubstituted mono-, di- or trinuclear aromatic $C_6$–$C_{14}$ hydrocarbon radical or a substituted or unsubstituted $C_4$–$C_{14}$ heterocyclic radical; R is hydrogen or a $C_1$–$C_5$ alkyl radical; each X substituent is independently selected from H, Cl, Br, $C_1$–$C_5$ alkyl and phenyl; and n is either 2, 3 or 4.

In the specification and claims, the terms $C_6$–$C_{14}$, $C_4$–$C_{14}$, $C_1$–$C_5$, $C_2$–$C_6$ represent radicals having, respectively, from 6 to 14, 4 to 14, 1 to 5 and 2 to 6 carbon atoms. The term "alkyl" is used herein to represent both straight and branched chain alkyl groups. Examples of aromatic $C_6$–$C_{14}$ hydrocarbon radicals are radicals of benzene, naphthalene, anthracene, phenanthrene and the like. The term "heterocyclic radicals" as used herein refers to ringed compounds in which the heteroatoms are selected from sulfur, oxygen and nitrogen. Examples of $C_4$–$C_{14}$ heterocyclic radicals are radicals of pyrrole, furan, thiophene, imidazole, oxazole, thiazole, quinoline, carbazole, pyridine and the like. The term "substituted" when used herein in reference to an aromatic $C_6$–$C_{14}$ radical or $C_4$–$C_{14}$ heterocyclic radicals refers to such radicals substituted with Cl, Br, $C_1$–$C_5$ alkyl or $C_2$–$C_6$ acyl moieties.

The invention's novel polyphenolic compounds are crystalline solids which are of low solubility in water and of moderate solubility in many organic solvents. These compounds have been found to have utility as branching agents in the production of randomly branched aromatic polycarbonates when copolymerized with difunctional phenols in simple, one-step processes.

This invention is also directed to novel thermoplastic randomly branched aromatic polycarbonate compositions based on a dihydric phenol and having an I.V. of 0.40 to 1.00 dl/g in methylene chloride at 25° C., wherein the branching component is a compound of formula I above. These novel polycarbonate compositions have excellent blow molding properties and are prepared by reacting a carbonate precursor, a difunctional phenol, and a compound of formula I above.

These novel polyphenolic compounds are obtained from the corresponding carbonyl precursors and monofunctional phenols under either acidic or alkaline condensing conditions, as shown by the following equation and as illustrated by the detailed procedures described in the examples:

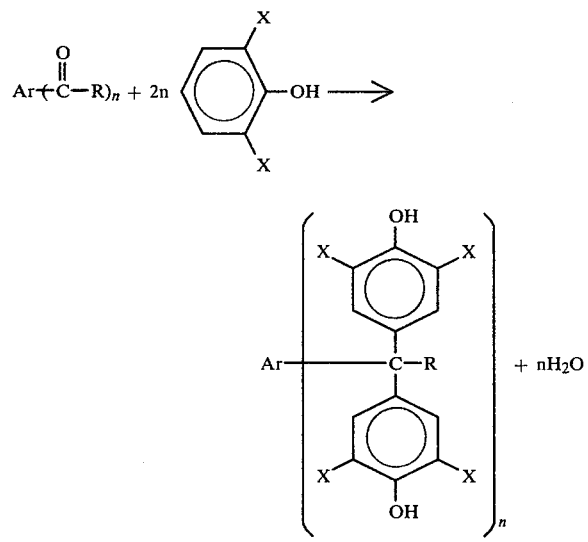

wherein the symbols Ar, R, X and n are as set forth above. When the reaction is carried out under acidic conditions, a catalyst containing the sulfhydryl (-SH) function may be employed. Examples of the sulfhydryl catalysts are ethanethiol, 1-butanethiol.thiophenol and mercaptoacetic acid.

The condensation reaction is best carried out by utilizing the phenolic reactant in excess of the stoichiometric amount. With phenols that are solid at ambient temperature, this method requires reaction temperatures near or above the melting point of the phenol that is used in excess. In addition, non-phenolic solvents, such as acetic acid, acetic anhydride, methylene chloride, can be used.

The reaction temperature encompasses ambient temperatures to elevated temperatures, such as 100° C. or higher. Although the reaction rate is faster at higher temperatures, there is also an increase in undesired by-products, such as isomeric polyphenols, which are less effective than the entirely p-substituted polyphenols in the copolymerization reaction with the diphenols.

The condensation reaction can be carried out either at atmospheric or superatmospheric pressures.

The progress of the condensation reaction can be monitored by chromatographic or spectroscopic methods. Since the reaction takes place stepwise, it becomes relatively easy to follow the formation of the di-, tetra-, hexaphenol, etc., stages, since there is a progressive increase in the gas chromatographic emergence times as the higher polyphenols are being formed.

The reaction can also be followed readily by infrared (ir) spectroscopy by the diminution or disappearance of the carbonyl band, a very strong, characteristic and diagnostic ir band, well suitable for qualitative and quantitative analysis.

Similarly proton nuclear magnetic resonance spectroscopy can sometimes be used at great advantage: an increase of resonance peaks in the aromatic region that are characteristic of the product, and not the precursor. can yield a readily available, quantitative information via integration of the specific aromatic and aliphatic region signals.

When X represents chlorine or bromine substituents, the novel polyphenols can also be prepared by direct halogenation, in solution or suspension, of the corresponding non-halogenated polyphenols. Methylene chloride, chloroform, acetic acid, water, other non-reactive liquids and aqueous sodium hydroxide solution may be used as solvents or dispersants. The degree of halogenation can readily be followed by gas or liquid chromatography, ir or proton nmr.

Purification of the novel polyphenolic compounds can be carried out by recrystallization, elution chromatography, or other methods known to those skilled in the art. Preferred solvents of recrystallization are methylene chloride, benzene, cyclohexane, methanol, ethanol and alcohol-water mixtures. Elution chromatography is carried out best over alumina or silica, using a variety of solvents as eluants.

The new polyphenolic compounds can be used for the preparation of branched polycarbonates. Another subject of the instant invention is, therefore, the novel, high molecular weight, branched polycarbonates which are substantially free of crosslinking.

In the preparation of the novel thermoplastic randomly branched polycarbonates of this invention, the amount of the polyphenolic compound which is reacted with the dihydric phenol and the carbonate precursor is critical to the extent that the amount employed must be sufficient to produce a true thermoplastic randomly branched polycarbonate which is substantially free of cross-linking. If an amount of polyphenolic compound employed is less than about 0.01 mole percent, based upon the moles of the dihydric phenol employed, the resulting polymer will not exhibit the degree of non-Newtonian melt characteristics desired for blow molding and/or melt extrusion purposes. Preferably, it is desirable to employ 0.01 to about 3.0 and more particularly, 0.01-1.0 mole percent of the polyphenolic compound, based upon the total moles of dihydric phenol.

The dihydric phenols that can be employed in the practice of this invention include bis(4-hydroxyphenyl)methane, 1,1-bis(4-hydroxyphenyl)ethane, 2,2-bis(4-hydroxyphenyl)propane, also called bisphenol-A or BPA, 2,2-bis(4-hydroxy-3-methylphenyl)propane, 3,3-bis(4-hydroxyphenyl)pentane, 2,2-bis(4-hydroxy-3-chlorophenyl)propane, 2,2-bis(4-hydroxy-3,5-dibromophenyl)propane, 1,1-bis(4-hydroxyphenyl)cyclohexane, p,p'-dihydroxydiphenyl, 3,3'-dichloro-4,4'-dihydroxydiphenyl, bis(4-hydroxyphenyl)ether, bis(4-hydroxyphenyl)sulfone, bis(3,5-dimethyl-4-hydroxyphenyl)sulfone, resorcinol, hydroquinone; 1,4-dihydroxy-2,5-dichlorobenzene, 1,4-dihydroxy-3-methylbenzene, bis(4-hydroxyphenyl)sulfoxide, bis(3,5-dimethyl-4-hydroxyphenyl)sulfoxide, and the like. A variety of additional dihydric phenols can also be employed such as are disclosed in U.S. Pat. Nos. 2,999,835, 3,028,365 and 3,153,008. It is, of course, possible to employ two or more different dihydric phenols or a copolymer of a dihydric phenol with glycol or with hydroxy or acid terminated polyester, or with a dibasic acid in the event a polycarbonate copolymer or interpolymer (copolyester-carbonate) rather than a homopolymer is desired for use in the preparation of the branched polymers of this invention. The preferred dihydric phenol is bisphenol-A.

The carbonate precursor employed can be either a carbonyl halide, a haloformate or a diaryl carbonate. Thus the carbonyl halides can be carbonyl chloride, carbonyl bromide, and mixtures thereof. The haloformates suitable for use include mono- or bishaloformates of dihydric phenols (bischloroformates of hydroquinone, monochloroformate of bisphenol-A etc.) or bishaloformates of glycols (bishaloformates of ethylene glycol, neopentyl glycol, polyethylene glycol, etc.). When using bishaloformates, equimolar amounts of free dihydric phenols are required to effect polymerization. When polymerizing monohaloformates of diphenols no free diphenol is required. While other carbonate precursors will occur to those skilled in the art, carbonyl chloride, also known as phosgene, is preferred.

The polymerization of dihydric phenols to high molecular weight polycarbonates may be carried out by any conventional method known in the art. For example, phosgene can be introduced into solution of the diphenol in organic bases, such as pyridine, triethylamine, dimethylaniline or into solutions of the diphenyl in suitable organic solvents, such as benzene, toluene, chlorobenzene, methylene chloride, carbon tetrachloride and the like, with the addition of acid binding agents.

In the most widely practiced polymerization process phosgene is introduced into an aqueous solution of the alkali metal salt of the diphenol in the presence of methylene chloride and a phase-transfer catalyst as well as a molecular weight regulator, usually a monofunctional phenol. One advantage of the instant invention is that the polyphenolic branching agent has the same reactivity profile as the diphenol used to make the linear chains, hence it can be added, in the desired amount, together with the diphenol at the beginning of the polymerization process. In other words, the polyphenolic compounds can be formulated directly into the reaction mixture to be polymerized to branched polycarbonates.

The reaction between the halogen containing carbonate precursor and the dihydric phenol and the polyfunctional phenol when carried out by the interfacial method in accordance with this invention is conducted in the presence of an inert organic solvent which is essentially immiscible with water and does not deleteriously affect the formed polymer. Examples of suitable organic solvents are methylene chloride, ethylene dichloride and chlorobenzene.

In a preferred variant of the polymerization process, the branching polyphenol is added in the form of an aqueous solution of its alkali metal salt. This is possible since the novel polyphenols of the instant invention are capable of forming stable aqueous solutions in the form of their alkali salts. The novel branching agent may also be formulated into the reaction mixture of the dihydric phenol to be polymerized in finely divided solid form or as a methylene chloride solution or slurry. In either form it is copolymerized readily in the polycarbonate forming process and becomes a fully incorporated segment of the polymer system.

The alkali metal hydroxide which can be employed in the polymerization process can be any of the alkali metal hydroxides selected from the groups consisting of the alkali group and alkaline earth groups. Specifically, these include potassium hydroxide, sodium hydroxide, lithium hydroxide, calcium hydroxide, magnesium hydroxide and the like.

The interfacial, or phase-transfer catalysts, which can be employed in the polymerization process can be any of the suitable catalysts that aid the polymerization of dihydric phenols with phosgene. Suitable catalysts include tertiary amines such as triethylamine, tripropylamine, N,N-dimethylaniline and the like; quaternary ammonium compounds such as tetraethylammonium chloride; cetyl triethyl ammonium bromide, tetra-n-heptylammonium iodide, tetra-n-propyl ammonium chloride, tetramethylammonium chloride, tetramethylammonium hydroxide, tetra-n-butylammonium iodide, benzyltrimethylammonium chloride and the like; and quaternary phosphonium compounds such as n-butyltriphenyl phosphonium bromide and tetrabutyl phosphonium chloride and the like.

The molecular weight regulators which can be employed in the interfacial process include monohydric phenols such as phenol, chroman-I [4-(2,4,4-trimethylchromanyl)phenol], p-t-butyl phenol, p-cumyl phenol, primary and secondary amines, and the like. Preferably phenol is employed as the molecular weight regulator.

It is sometimes desirable to introduce reducing agents, such as sodium dithionite into the aqueous system in order to supress the formation of colored contaminants.

The aqueous interfacial polymerization method may be carried out at temperatures from ambient to about 50° C. However, higher temperatures are within the scope of this invention since the instant method is not temperature dependent.

The diphenol-polyphenol mixture can be converted into branched polycarbonates also by esterification with dialkyl, alkyl-aryl or diaryl carbonates at elevated temperatures from about 50° C. to about 325° C., at atmospheric or at reduced pressure, in neat form, or in the presence of neutral diluents or in the presence of transesterification catalysts, such as metal oxides, hydroxides, carbonates and the like, as known in the art. When using aryl carbonates, phenols are generated in the transesterification process, so that no molecular weight regulators need be added to the reaction mixture. In fact, the degree of polymerization is controlled by the extent of removal of the monohydroxylic coproducts, such as alcohols or phenols.

The branched polycarbonates, when produced according to the instant invention by the interfacial polymerization technique, were recovered from the washed, neutral methylene chloride phase by steam precipitation and drying and were fed into an extruder operating at 265° C. and the extrudates were comminuted into pellets. When prepared by the transesterification method, the polycarbonate melt was directly converted into extrudate and pellets.

While some of the physical-mechanical measurements can be carried out directly with the polycarbonate powder or pellets, some tests require molded specimens. To provide these, the pellets are injection molded at about 315° C. into test bars according to the dimensions required by the test method, such as the notched Izod impact test carried out according to ASTM D-256.

The following test procedures were utilized:

Intrinsic viscosity (I.V.) was determined in methylene chloride solution at 25° C. and is given as deciliters per gram (dl/g).

Molecular weight determinations (number average, $M_n$; weight average, $M_w$ and Z-average, $M_z$) were carried out on Waters Associates GPC Model 200, in methylene chloride solution.

Modified melt flow (K.I.) values, expressed in centiseconds, were obtained by an automated ASTM D-1238 procedure at 300° C. on a Tinius Olsen Melt Indexer, Model T-3, Condition 0.

Melt index ratio (M.I.R.), which is the ratio of melt flow rates at two different shear levels, and is a measure of the non-Newtonian property of the polymer, was obtained on the Tinius Olsen Melt Indexer described above. The M.I.R. values of linear Newtonian polycarbonates are typically less than 1.4, while those of the branched polycarbonates are typically higher than 1.5.

The branched polycarbonates produced according to the instant invention are soluble in selected organic solvents and can be worked into shaped articles from solutions, such as into films. Being thermoplastic, these branched polycarbonates can be easily fabricated by conventional shaping methods from melt, such as by extrusion, molding, blow-molding, lamination and the like.

It is also regarded to be among the features of this invention to include in the composition other ingredients such as fillers, mold release agents, pigments, dyestuffs, stabilizers and the like, in conventional amounts for their conventionally employed purposes.

DESCRIPTION OF THE PREFERRED EMBODIMENT

The following examples are set forth to illustrate the invention and are not to be construed to limit the scope of the invention. The product polyphenolic compounds are identified by ir and nmr.

EXAMPLE 1

Preparation of the novel tetraphenol: $\alpha, \alpha, \alpha', \alpha'$-tetrakis(4-hydroxyphenyl)-1,4-diethylbenzene.

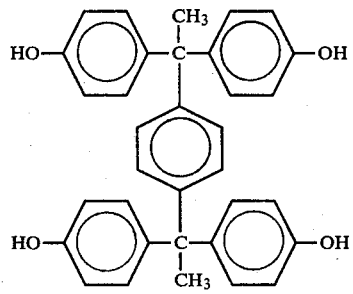

Into a molten mixture of 188g of phenol and 24.3g of p-diacetylbenzene (m.p. 112°-113° C.), there was introduced hydrochloric acid gas at 50° C. until the separation of solids was complete. The crystalline precipitate was filtered off through a sintered glass funnel and the filtercake rinsed with methylene chloride until phenol-free. The novel colorless, crystalline tetraphenol was 100% pure by gas chromatographic analysis and had a melting point of 307°-308° C. Stripping of the phenolic mother liquor and the methylene chloride washing yielded a solid residue. Ir and nmr spectra were consistent with the structure shown above.

EXAMPLE 2

Preparation of a polycarbonate branched with $\alpha, \alpha, \alpha', \alpha'$-tetrakis(4-hydroxyphenyl)-1,4-diethylbenzene.

To a well stirred mixture of 2283g (10 moles) of 2,2-bis(4-hydroxyphenyl)propane, (BPA), 7000 ml of methylene chloride, 5500ml of water, 31.1g (0.33 mole) of phenol, 20.2g (0.02 mole) of triethylamine and enough 45% aqueous sodium hydroxide solution to maintain a pH of 11.5, there was added a clear, colorless solution of 10.05g (0.020 mole) of the $\alpha, \alpha, \alpha', \alpha'$-tetrakis(4-hydroxyphenyl)-1,4-diethylbenzene, prepared in accordance with Example 1, in 30% aqueous sodium hydroxide. The introduction of phosgene into the well stirred reaction mixture was carried out at a rate of 30g/minute for 47 minutes, continuously adjusting the pH to remain between 11.1 and 11.8, until the BPA content of the aqueous phase was reduced to 8 parts per million.

The recovered polycarbonate from the washed, neutral methylene chloride phase by steam precipitation and drying had the following properties: I.V. 0.606 dl/g; $M_n$ 16,500; $M_w$ 44,000; $M_z$ 81,000; K.I. 16,700 csec.; M.I.R. 2.35 and notched Izod impact 16.4 ft. lb.

EXAMPLE 3

Preparation of the novel tetraphenol $\alpha, \alpha, \alpha', \alpha'$-tetrakis(4-hydroxyphenyl)-1,3-diethyl-5-acetylbenzene.

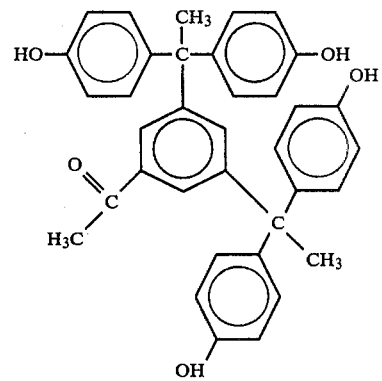

The procedure of Example 1 was repeated, except that 30.6g (0.15 mole) of 1,3,5-triacetylbenzene (m.p. 160°-162° C.) was substituted for the diacetylbenzene. When gas chromatographic analysis of a sample taken from the reaction mixture indicated that the formation of the tetraphenol was essentially complete, the excess phenol was stripped off in aspirator vacuum to yield a solid residue which, after recrystallization from methanol, yielded yellowish white crystals of $\alpha, \alpha, \alpha', \alpha'$-tetrakis(4-hydroxyphenyl)-1,3-diethyl-5-acetylbenzene, m.p. 144°-6° C., that were 96% pure by gas chromatography.

EXAMPLE 4

Preparation of a branched polycarbonate with a tetraphenol of Example 3.

The procedure of Example 2 was exactly repeated except that the tetraphenol described in Example 1 was replaced with 10.9g (0.020 mole) of the $\alpha, \alpha, \alpha', \alpha'$-tetrakis(4-hydroxyphenyl)-1,3-diethyl-5-acetylbenzene of Example 3, in the form of its aqueous sodium hydroxide solution. The branched polymer, recovered by steam precipitation, had the following characteristics: I.V. 0.611; $M_n$ 15,800; $M_w$ 47,000; $M_z$ 74,000; K.I. 17,100; M.I.R. 2.51 and notched Izod impact 15.7 ft. lb.

EXAMPLE 5

Preparation of the novel tetraphenol 60, $\alpha, \alpha', \alpha'$-tetrakis(4-hydroxy-3-methylphenyl)-1,3-diethylbenzene.

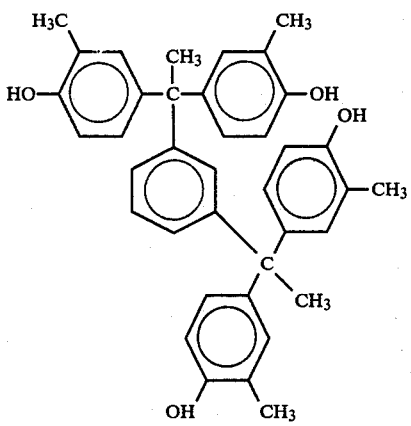

The procedure of Example 1 was repeated except that phenol was replaced with 212g of o-cresol, the 1,4-diacetylbenzene was replaced with the same amount of 1,3-diacetylbenzene (m.p. 32°–34° C.) and a small amount (1 ml) of 1-butanethiol was added as a condensation catalyst prior to the introduction of HCl gas. When ir and gc indicated the disappearance of the starting diketone, the reaction mixture was stripped of phenol and the solid, orange-yellow glass was recrystallized from cyclohexane to yield white crystals, m.p. 123°–7° C., that were 89% pure by gc and identified as the title compound.

EXAMPLE 6

Preparation of a branched polycarbonate with the tetraphenol of Example 5.

The procedure of Example 2 was exactly repeated except that the tetraphenol of Example 1 was replaced with an aqueous solution of the sodium salt of 14.0g (0.025 mole) of the $\alpha, \alpha, \alpha', \alpha'$-tetrakis(4-hydroxy-3-methylphenyl)-1,3-diethylbenzene of Example 5.

The branched polymer had the following properties: I.V. 0.703; $M_n$ 15,000; $M_w$ 49,300; $M_z$ 94,400; K.I. 51,200; M.I.R. 2.42 and notched Izod impact of 15.3 ft. lb.

EXAMPLE 7

Preparation of the novel tetraphenol $\alpha, \alpha, \alpha', \alpha'$-tetrakis(4-hydroxy-3-methylphenyl)-p-xylene.

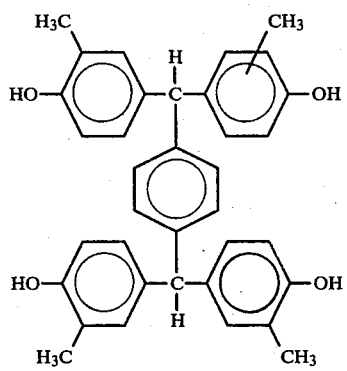

The procedure of Example 1 was exactly repeated except that phenol was replaced with 212g of o-cresol and 1,4-diacetylbenzene was replaced with 20.1g (0.15 mole) of terephthaldicarboxaldehyde, m.p. 115°–116° C. The formation of the tetraphenol was very facile, as shown by its precipitation from the reaction mixture within 10 minutes after the introduction of HCl gas. Workup, after ca. 3 hours of standing at 35° C., by filtration and recrystallization, with charcoaling, of the filter cake yielded slightly pale yellow crystals (m.p. 195°–196.5° C.) that were 97.9% pure by gas chromatography and were identified as $\alpha, \alpha, \alpha', \alpha'$-tetrakis(4-hydroxy-3-methylphenyl)-p-xylene.

EXAMPLE 8

Preparation of a branched polycarbonate from 2,2-bis(4-hydroxy-3-chlorophenyl)propane with the tetraphenol of Example 7.

The procedure illustrated in Example 2 was exactly repeated, except that BPA was replaced with 2972g (10 moles) of 2,2-bis(4-hydroxy-3-chlorophenyl)propane and the tetraphenol was replaced with 10.6g (0.020 mole) of the $\alpha, \alpha, \alpha', \alpha'$-tetrakis(4-hydroxy-3-methylphenyl)-p-xylene of Example 7. The polycarbonate obtained had the following properties: I.V. 0.618; $M_n$ 20,450; $M_w$ 54,710; $M_z$ 92,400; K.I. 22,900 and M.I.R. 2.24.

EXAMPLE 9

Preparation of the novel hexaphenol $\alpha, \alpha, \alpha', \alpha', \alpha'', \alpha''$-hexakis(4-hydroxyphenyl)-1,3,5-triethylbenzene.

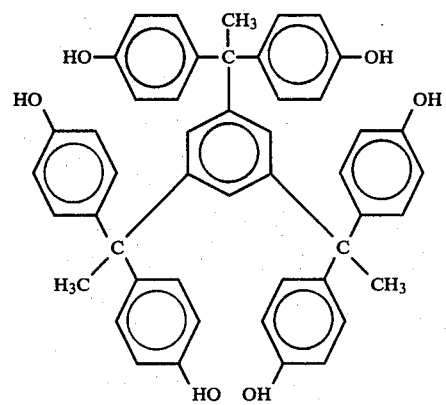

The procedure of Example 1 was exactly repeated, except that the diacetylbenzene was replaced with 81.6g of $\alpha, \alpha, \alpha', \alpha'$-tetrakis(4-hydroxyphenyl)-1,3-diethyl-5-acetylbenzene (the product of Example 3) and 1 ml of thioglycolic acid was added, prior to the introduction of hydrochloric acid gas, as a cocatalyst. After a small sample taken from the reaction mixture indicated by ir and gc that the starting material had all disappeared and the hexaphenol formation was complete, the entire reaction product was stripped of phenol via a water aspirator vacuum and the solid, slightly off-colored product was purified by recrystallization from aqueous methanol. The white crystals were 91% pure by gc and had a m.p. of 172°–8° C.

EXAMPLE 10

Preparation of a branched polycarbonate with the hexaphenol of Example 9.

The procedure of Example 2 was repeated, except that the tetraphenol was replaced with 10.7g (0.015 mole) of the hexaphenol prepared according to Example 9. The polycarbonate powder had the following properties: I.V. 0.609; $M_n$ 19,050; $M_w$ 47,000; $M_z$ 68,700;

K.I. 19,600; M.I.R. 2.74; and notched Izod impact of 16.6 ft. lb.

Structurally depicted below are additional examples of novel polyphenolic compounds which can be prepared by the procedures as generally set forth herein:

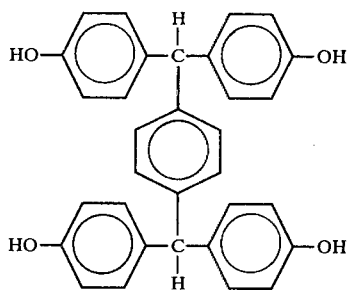

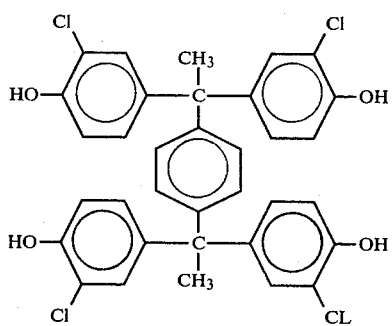

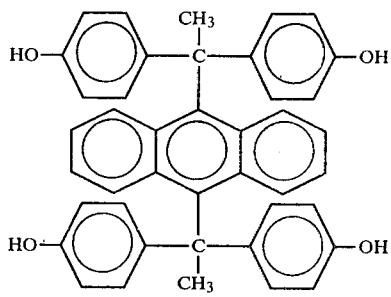

What is claimed is:

1. A high molecular weight, thermoplastic, branched polycarbonate composition, based on a dihydric phenol, having an intrinsic viscosity of about 0.40 to 1.00 dl/g in methylene chloride at 25° C. wherein the branching component is derived from a polyphenolic compound of the formula

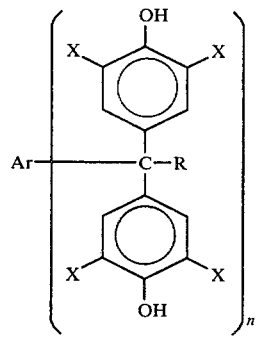

2. The composition of claim 1 wherein the branching component is $\alpha, \alpha, \alpha', \alpha'$-tetrakis(4-hydroxyphenyl)-1,4-diethylbenzene.

3. The composition of claim 1 wherein the branching component is $\alpha, \alpha, \alpha', \alpha'$-tetrakis(4-hydroxyphenyl)-1,3-diethyl-5-acetylbenzene.

4. The composition of claim 1 wherein the branching component is $\alpha, \alpha, \alpha', \alpha'$-tetrakis(4-hydroxy-3-methylphenyl)-1,3-diethylbenzene.

5. The composition of claim 1 wherein the branching component is $\alpha, \alpha, \alpha', \alpha'$-tetrakis(4-hydroxy-3-methylphenyl)-p-xylene.

6. The composition of claim 1 wherein the branching component is $\alpha, \alpha, \alpha', \alpha', \alpha'', \alpha''$-hexakis(4-hydroxyphenyl)-1,3,5-triethylbenzene.

* * * * *

UNITED STATES PATENT AND TRADEMARK OFFICE
CERTIFICATE OF CORRECTION

PATENT NO. : 4,426,513
DATED : January 17, 1984
INVENTOR(S) : Victor Mark

It is certified that error appears in the above-identified patent and that said Letters Patent are hereby corrected as shown below:

Column 7, line 68     -     "(0.02 mole)" should be "(0.2 mole)"

Column 12 after first formula - a formula is missing

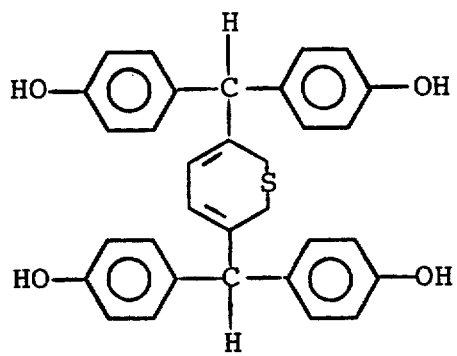

UNITED STATES PATENT AND TRADEMARK OFFICE
CERTIFICATE OF CORRECTION

PATENT NO. : 4,426,513

DATED : January 17, 1984

INVENTOR(S) : Victor Mark

It is certified that error appears in the above-identified patent and that said Letters Patent are hereby corrected as shown below:

Column 12, claim 1 - bottom of claim after formula is missing

"wherein Ar is a mono, -di- or trinuclear aromatic $C_{6-14}$ hydrocarbon radical, R is hydrogen or a $C_{1-5}$ alkyl radical; each X is independently selected from hydrogen, chloro, bromo, $C_1$-$C_5$ alkyl and phenyl; and n is 2, 3, or 4."

Signed and Sealed this

Fifteenth Day of October 1985

[SEAL]

Attest:

Attesting Officer

DONALD J. QUIGG

Commissioner of Patents and Trademarks—Designate